United States Patent [19]

DeGonia et al.

[11] Patent Number: 4,966,720

[45] Date of Patent: Oct. 30, 1990

[54] OIL SOLUBLE SULFURIZED OLEFINS AND TWO TEMPERATURE ZONE PROCESS FOR THEIR PREPARATION

[75] Inventors: David J. DeGonia, Granite City; Paul G. Griffin, Collingsville, both of Ill.

[73] Assignee: Ethyl Petroleum Additives, Inc., St. Louis, Mo.

[21] Appl. No.: 517,486

[22] Filed: Apr. 30, 1990

Related U.S. Application Data

[63] Continuation of Ser. No. 304,762, Jan. 31, 1989, abandoned.

[51] Int. Cl.$^5$ ............... C10M 135/04; C10M 135/22
[52] U.S. Cl. ......................................... 252/45; 568/18
[58] Field of Search ......................... 252/45; 568/18

[56] References Cited

U.S. PATENT DOCUMENTS

| | | | |
|---|---|---|---|
| 2,565,493 | 8/1951 | Gardner | 260/139 |
| 2,708,199 | 5/1955 | Eby | 260/327 |
| 3,410,800 | 11/1968 | Ford et al. | 252/48.8 |
| 3,471,404 | 10/1969 | Myers | 252/45 |
| 3,697,499 | 10/1972 | Myers | 260/139 |
| 4,204,969 | 5/1980 | Papay et al. | 252/45 |
| 4,563,302 | 1/1986 | Griffin et al. | 252/45 |
| 4,645,610 | 2/1987 | Born et al. | 252/45 |
| 4,710,273 | 12/1987 | Okamoto | 203/29 |

Primary Examiner—Olik Chaudhuri
Assistant Examiner—Jerry D. Johnson
Attorney, Agent, or Firm—David M. Bunnell

[57] ABSTRACT

Sulfurized olefins such as isobutylene which are soluble in hydrotreated oils are prepared by reacting a basic, aqueous alcoholic solution of sodium sulfide with an adduct formed by adding olefin to sulfur monochloride at low temperatures until the mole ratio of olefin to sulfur monochloride is between about 1.7–1.9 to 1.

11 Claims, No Drawings 4,966,720

OIL SOLUBLE SULFURIZED OLEFINS AND TWO TEMPERATURE ZONE PROCESS FOR THEIR PREPARATION

This application is a continuation of application Ser. No. 304,762, filed Jan. 31, 1989 now abandoned.

BACKGROUND OF THE INVENTION

This invention relates generally to sulfurized olefins useful as EP additives in lubricating oils and more specifically to a two-stage process for making sulfurized olefins having improved oil solubility in which a first stage adduct of olefin and sulfur monochloride having a 1.7 to 1.9:1 mole ratio of olefin to sulfur monochloride is formed at controlled low temperatures and then reacted with sodium sulfide.

Sulfurized olefins are well-known additives for use in lubricating oils. One method of preparing such materials involves a two-stage reaction process where in the first stage the olefin, such as isobutylene, is added to sulfur monochloride to form an adduct The reaction is exothermic and is usually carried out at temperatures of 20°–80° C. and preferably between about 50°–60° C. In practice, the olefin is added until the reaction stops as indicated by the loss of exotherm. Preferred amounts of from about 1.5 to 2.2 gram moles of olefin per mole of sulfur monochloride have been disclosed but the reaction is self-limiting due to the loss of HCl from the product and a typical self-limiting ratio is about 1.7 to 1. The first stage adduct is then reacted with sodium sulfide and sulfur in an aqueous, alkanol reaction medium at temperatures of from about 50° C. up to reflux. The resulting products are useful EP additives which are soluble in mineral oils but not in hydrotreated oils. The preparation of organic polysulfides from adducts made by reacting an olefin having from at least six to about 30 carbon atoms with about a stoichiometric equivalent of a sulfur halide at a temperature of from about 0° C. to 50° C. is disclosed in U.S. Pat. No. 2,708,199. We have now discovered a novel, low temperature process for preparing hydrotreated oil soluble, sulfurized olefins.

SUMMARY OF THE INVENTION

In accordance with this invention, there is provided a process for making a sulfurized olefin having improved solubility in lubricating oil which comprises:

A. reacting sulfur monochloride with an aliphatic monoolefin containing 3 to 6 carbon atoms to form an adduct by pre-cooling sulfur monochloride to a temperature below about 10° C. and adding said monoolefin to the sulfur monochloride with cooling so as to maintain the temperature of the reaction mixture at or below about 10° C. until from about 1 to 1.5 gram moles of said monoolefin per gram mole of sulfur monochloride have been added and then adding additional monoolefin while maintaining said temperature at from about 15° to 22° C. until a total of from about 1.7 to 1.9 gram moles of said monoolefin per gram mole of sulfur monochloride have been added;

B. reacting said adduct with a basic, aqueous alcoholic solution of sodium sulfide at a temperature of from about 50° C. up to reflux to form said sulfurized olefin; and C. recovering said sulfurized olefin.

Also provided are the sulfurized olefin made by the foregoing process and lubricating oils containing the sulfurized olefin.

DETAILED DESCRIPTION

Useful olefins for use in forming the sulfurized olefins are the monoethylenically unsaturated aliphatic hydrocarbons containing 3 to about 6 carbon atoms. These include 1-butene, 2-butene, isobutene, 1-pentene, 2-pentene, 2-methyl-1-butene, 3-methyl-1-butene, 2-methyl-2-butene, hexenes, 2-methyl-2-pentene, 2-ethyl-2-butene and the like including mixtures thereof.

Preferably the olefins are branched-chain olefins such as isobutene, 2-methyl-1-butene, 2-methyl-2-butene, and the like. More preferably the ethylenic double bond adjoins a tertiary carbon atom such as in isobutylene, the most preferred olefin.

The first stage reaction to form the sulfur monochloride-olefin adduct is exothermic and is conducted by adding the olefin to the sulfur monochloride. The olefin can be added as a gas or liquid.

The sulfur monochloride is first added to a reactor which is equipped with an adequate cooling system and agitator to maintain the reaction mixture within the prescribed low temperature ranges during the olefin addition. The sulfur monochloride is pre-cooled to at least 10° C. and, preferably, to 0° C. to 5° C. prior to beginning the olefin addition. No solvent or catalyst, such as an alcohol promotor, is needed for the reaction to proceed in a satisfactory manner to provide the desired product It is important to keep the temperature of the reaction mixture below about 10° C. until from about 60 to 80 weight percent of the total amount of olefin has been added (about 1.0 to 1.5 gram moles of olefin per gram mole of sulfur monochloride) in order to minimize the formation of high molecular species which adversely effect the oil solubility of the sulfurized olefin product. The coolant flow and rate of olefin addition are adjusted to maintain the proper temperature. After about 60 to 80 percent of the olefin has been added, the temperature can be allowed to rise to between about 15° to 22° C. without adversely effecting final product quality so that a practical, economic process is provided. The low temperatures of the reaction reduce the amount of side reactions caused by splitting off HCl. The reaction is not run to completion as in the case of adduct formation at higher temperatures, e.g. 50°–60° C., where olefin addition is continued until a loss of exotherm is noted and/or unreacted olefin is vented from the reactor. According to the process of this invention, olefin addition is stopped after the addition of from about 1.7 to 1.9 gram moles of olefin per gram mole of sulfur monochloride, and preferably after about 1.85±0.03 gram moles of olefin per gram mole of monochloride have been added. This end point can be determined by monitoring the specific gravity of the mixture using a commercially available device (for isobutylene, specific gravities of from about 1.170–1.174 at 26° C. correspond to the desired amount of olefin in the adduct). Using amounts of olefin above or below the prescribed molar ratio range results in a higher viscosity sulfurized olefin product which adversely impacts the solubility of the product in hydrotreated oils. After olefin addition is completed, the temperature can be permitted to rise to ambient temperatures e.g. up to 35° C.

The first stage reaction should be conducted for a time sufficient to complete the reaction between sulfur monochloride and olefin. This is usually limited by heat removal and the olefin feed rate is controlled to hold the temperature within the desired range. The overall time required to complete the reaction depends upon the scale of the process and can vary from a few minutes up to 12 or more hours. The time is not critical.

During the first stage reaction, HCl gas is evolved and means are provided to scrub the gas vented from the reactor to remove HCl prior to releasing the vent gas to the atmosphere.

In the second stage reaction to produce the sulfurized olefin product, the liquid first stage adduct is reacted with a sodium sulfide, $Na_2S_x$ ($Na_2S+S$) where x is 1 to 4, preferably in a slightly basic (pH 8 to 12) aqueous, alcoholic medium. The second stage is preferably carried out by charging aqueous sodium sulfide ($Na_2S$), water, alkanol and elemental sulfur flowers to a jacketed reactor equipped with agitator and cooling coils and then gradually adding the adduct to the mixture which has been heated to the initial reaction temperature.

The sodium sulfide may be obtained from any of a number of sources. For example, it can be made by mixing approximately equal molar amounts of sodium hydrosulfide and sodium hydroxide. If hydrogen sulfide is available, it can be adsorbed in aqueous NaOH to form a solution of sodium sulfide and/or sodium hydrosulfide, depending upon the amount of hydrogen sulfide adsorbed. Whatever the source, the resulting solution should be adjusted with either NaOH, NaSH or $H_2S$ so that the resulting solution consists mainly of sodium sulfide.

The amount of sodium sulfide can vary somewhat. For example, from about 1.0 to 3.0 gram mole for each gram mole of first stage adduct and preferably from about 1.0 to 1.6 gram mole of sodium sulfide for each gram mole of first stage adduct.

The amount of water can vary widely without detrimental effect. Good results can be obtained using about 0.5 to 2.5 gram moles of water per gram mole of adduct. This includes water added as such, water in aqueous reactants and water which might be formed by reaction of hydrogen sulfide or sodium hydrosulfide with sodium hydroxide in forming a sodium sulfide solution.

Alcohol is required in the second stage reaction. Preferably, these are lower alcohols containing 1-4 carbon atoms such as methanol, ethanol, n-propanol, n-butanol, isobutanol, tert-butanol and the like, including mixtures thereof. The preferred alcohol is isopropanol either alone or mixed with other alkanols such as tert-butanol.

The amount of alcohol can likewise vary over a wide range. A useful range is about 0.2 to 1.5 parts by weight per each part by weight of adduct. A more preferred range is about 0.4 to 0.7 parts by weight alcohol per each part by weight adduct.

The preferred amount of sulfur added is 0 to 1.0 gram atom for each gram mole of first stage adduct More preferably 0.05 to 0.50 gram atom of sulfur is used per gram mole of adduct, and most preferably 0.05 to 0.25 gram atom is used per gram mole of adduct.

In a preferred mode of operation the mixture of sodium sulfide, sulfur and aqueous alkanol is stirred and heated to reaction temperature and then the adduct is continuously added to it. However, the reaction can be carried out in other ways such as by adding the sodium sulfide, sulfur, and aqueous alkanol mixture to the adduct or by mixing everything together and heating the mixture.

Preferred second stage reaction temperature is about 50° C. up to reflux temperature. A more preferred reaction temperature is about 75°-85° C.

After all of the adduct has been added to the sodium sulfide/sulfur/aqueous alkanol mixture, which is usually completed in about 1-8 hours, the mixture is preferably heated to just below reflux for about 2-8 hours to assure completion of the reaction.

A convenient way in which to make an effective sulfurized isobutylene is to base the amount of NaHS, NaOH, sulfur, alcohol and water used on the amount of $S_2Cl_2$-isobutylene adduct. Following this procedure, preferably, the mole ratio of NaHS to adduct ranges from about 1.1 to 1.8:1; the mole ratio of NaOH to adduct from about 0.6 to 1.2:1; the mole ratio of sulfur to adduct from about 0.05 to 0.25; the weight ratio of water to adduct from about 0.7 to 1.7:1; and the weight ratio of alcohol to adduct from about 0.4 to 0.7:1. The ratios can be varied to control the sulfur content so as to obtain the desired amount of sulfur in the product which is, preferably, about 44 to 48 weight percent sulfur.

After reaction of the adduct with the sodium sulfide and sulfur mixture, the product is recovered by conventional methods, by distilling off alkanol, water washing and filtering.

The invention is further illustrated by, but is not intended to be limited to, the following examples wherein parts are parts by weight unless otherwise indicated.

EXAMPLE 1

Into a glass lined, jacketed reaction vessel equipped with an agitator and a refrigerated cooling system place 5080 Kgs of sulfur monochloride and cool the sulfur monochloride to a temperature of about 0° C. With stirring and cooling of the sulfur monochloride at atmospheric pressure, add isobutylene below the surface of the sulfur monochloride at a rate of about 650 to 975 Kgs per hour. The reaction will exotherm to 8°-10° C. After about 2420 Kgs of isobutylene is charged (62%), adjust the cooling rate to provide a reaction temperature of about 20° C.±2° C. while continuing to add isobutylene until the specific gravity of the reaction mixture is about 1.73±0.05 at 26° C. (1.85±0.03 gram moles of olefin per gram mole of sulfur monochloride) at which point a total of about 3900 Kgs of isobutylene have been added The HCl evolved is removed from the off-gas by alkaline scrubbing. After completion of the isobutylene addition, the reaction is finished, and the batch is ready to be utilized in the second stage.

In a separate jacketed reaction vessel equipped with an agitator and cooling coils are placed 3700 Kgs of water which is heated to about 20° C., 3960 Kgs of a 3 to 1 by weight mixture of isopropanol and tertiary-butanol, 4910 Kgs of NaHS (45% in aqueous solution), 2140 Kgs of 50% by weight commercial grade NaOH and 126 Kgs of elemental sulfur. About 0.5 Kg of a defoamer is also included in the initial charge. The foregoing mixture is heated to about 50° C. and the adduct from stage 1 (7470 Kgs) is added to the reaction vessel over about a 2½ hour period with stirring with the reaction mixture being allowed to exotherm to about 70° C. and then is maintained at about 78±3° C. at atmospheric pressure until the adduct addition is complete. The reaction is then heated to alcohol reflux temperature (82° C.) and refluxed for about 3 hours. The $H_2S$ evolved is removed by caustic scrubbing. After reflux, the alcohol is stripped at atmospheric pressure by applying steam to the reactor coils until the temperature reaches 90° C. and then vacuum is applied to remove the remaining alcohol. The distilled alcohol containing residual sulfur compounds is stored for re-use. Process water 11,760 Kgs is added to the reactor with agitation and heated to 60°–65° C. in order to wash the organic layer after which agitation and heating is stopped and the mixture separates into an organic phase and a brine layer. The lower aqueous brine layer is removed. Water containing residual sulfur is stripped from the organic layer (100 mm Hg, 100°–110° C.) and recycled. Vacuum is broken with nitrogen and the product is then filtered using a filter aid. The product is a light colored oil having a kinematic viscosity at 100° C. of 6.0 cst. and a copper corrosion test (CCT) result of about 60. The product composition contains about 48% sulfur, and 0.61% chlorine.

Product prepared according to the process of Example 1 was dissolved in a severely hydrotreated basestock oil (Petro-Canada 85W140) to provide a 5% by weight solution. The solution remained clear after standing at room temperature (about 25° C.) for four weeks. In contrast, a sulfurized olefin product was prepared by a similar adduct sulfurization reaction but from an adduct formed by a reaction in which the sulfur monochloride was not pre-cooled and the reaction mixture was allowed to exotherm to 55°–60° C. during the first few minutes of isobutylene addition and then maintained at 55°–60° C. using external cooling. This product, when added at a 5% by weight level to the hydrotreated basestock oil, provided a very hazy mixture which remained that way after standing for four weeks at room temperature. Kinematic viscosity and gel permeation chromatography (GPC) determinations on the materials showed that the high temperature adduct contains more high molecular weight cross-linking structures than the low temperature adduct which structures apparently cause the higher viscosity and poor solubility characteristics of the final sulfurized olefin products.

A product prepared according to the process described in Example I was compared to a product prepared by a similar process except that in the adduct preparation the temperature was allowed to exotherm immediately to 20° C. rather than being held below 10° C. until at least about 60–70% by weight of the isobutylene charge had been added. The adduct showed a significantly higher quantity of undesirable high molecular weight structures by gel permeation chromatography (average area % 6.67 vs. 5.01 for the adduct prepared according to the process of the invention). The final product also had a higher viscosity (7.57 cst. at 100° C. vs. 6.47 cst.). Although both products were soluble at 5% by weight in the hydrotreated basestock, the product of the invention exhibits improved solubility in basestock in which product solubility is even more difficult, for example synthetic oils (PAO).

The sulfurized olefins of the inventions are especially useful in lubricating oil formulations used in gear applications. In this use, the sulfurized olefin is added, for example to a mineral oil or a hydrotreated base stock oil, in an amount sufficient to improve the EP property of the lubricant. An amount of from about 0.1 to 10.0 weight percent in the base oil is usually sufficient.

Fully formulated gear lubricants include other conventional additives which perform various functions. Examples of such additives are corrosion inhibitors for ferrous and non-ferrous metals, such as tetrapropenyl succinic acid and bis-(2,5-alkyldithia)-1,3,4-thiadiazoles and antiwear additives such as alkyl or aryl phosphonates, phosphites, thiophosphates, dithiophosphates, phosphoric acids, zinc dialkyl or diaryl dithiophosphate, chlorinated hydrocarbons, and sulfurized fatty esters and amines.

We claim:

1. A process for making a sulfurized olefin having improved solubility in lubricating oil comprising:
   A. reacting sulfur monochloride with an aliphatic monoolefin containing 3 to 6 carbon atoms to form an adduct by pre-cooling sulfur monochloride to a temperature below about 10° C. and adding said monoolefin to the sulfur monochloride with cooling so as to maintain the temperature of the reaction mixture at or below about 10° C. until from about 1 to 1.5 gram moles of said monoolefin per gram mole of sulfur monochloride have been added and then adding additional monoolefin while maintaining said temperature at from about 15° to 22° C. until a total of from about 1.7 to 1.9 gram moles of said monoolefin per gram mole of sulfur monochloride have been added;
   B. reacting said adduct with a basic, aqueous alcoholic solution of sodium sulfide at a temperature of from about 50° C. up to reflux to form said sulfurized olefin; and
   C. recovering said sulfurized olefin.

2. The process of claim 1 wherein said monoolefin is a branched chain monoolefin.

3. The process of claim 2 wherein said olefin is isobutylene, the sulfur monochloride is pre-cooled to a temperature of from about 0° to 5° C., the reaction mixture is maintained at a temperature of from about 0° C. to 10° C. until about 60 weight percent of the total amount of said isobutylene has been added and the temperature is thereafter maintained at about 20° C.±2° C. until a total of from about 1.82 to 1.88 moles of said isobutylene per gram mole of sulfur monochloride have been added.

4. A sulfurized lubricating oil additive having improved solubility made by the process comprising:
   A. reacting sulfur monochloride with an aliphatic monoolefin containing 3 to 5 carbon atoms to form an adduct by pre-cooling sulfur monochloride to a temperature below about 10° C. and adding said monoolefin to the sulfur monochloride with cooling so as to maintain the temperature of the reaction mixture at or below about 10° C. until from about 1.0 to 1.5 gram moles of said monoolefin per gram mole of sulfur monochloride have been added and then adding additive monoolefin while maintaining said temperature at from about 15° to 22° C. until a total of from about 1.7 to 1.9 gram moles of said monoolefin per gram mole of sulfur monochloride have been added;
   B. reacting said adduct with a basic, aqueous alcoholic solution of sodium sulfide at a temperature of from about 50° C. up to reflux to form said sulfurized olefin; and
   C. recovering said sulfurized olefin.

5. A sulfurized additive of claim 4 wherein said monoolefin is a branched chain monoolefin.

6. A sulfurized additive of claim 5 wherein said olefin is isobutylene, the sulfur monochloride is pre-cooled to a temperature of from about 0° to 5° C., the reaction mixture is maintained at a temperature of from about 8° to 10° C. until about 60 weight percent of the total amount of said isobutylene has been added and the temperature is thereafter maintained at about 20° C.±2° C. until a total of from about 1.82 to 1.88 moles of said isobutylene per gram mole of sulfur monochloride have been added.

7. A lubricating oil composition containing from about 90.0 to 99.9 percent by weight of an oil of lubricating viscosity and from about 0.1 to 10.0 percent by weight of the sulfurized, additive according to claim 4.

8. A lubricating oil composition according to claim 7 wherein said oil is a hydrotreated oil.

9. A lubricating oil composition containing from about 90.0 to 99.9 percent by weight of an oil of lubricating viscosity and from about 0.1 to 10.0 percent by weight of the sulfurized additive according to claim 6.

10. A lubricating oil composition according to claim 9 wherein said oil is a hydrotreated oil.

11. A sulfurized additive of claim 4 wherein said monoolefin is selected from the group consisting of 1-butene, 2-butene, isobutene, 1-pentene, 2-pentene, 2-methyl-1-butene, 3-methyl-1-butene, and 2-methyl-2-butene and mixtures thereof.

* * * * *